Figure 1:
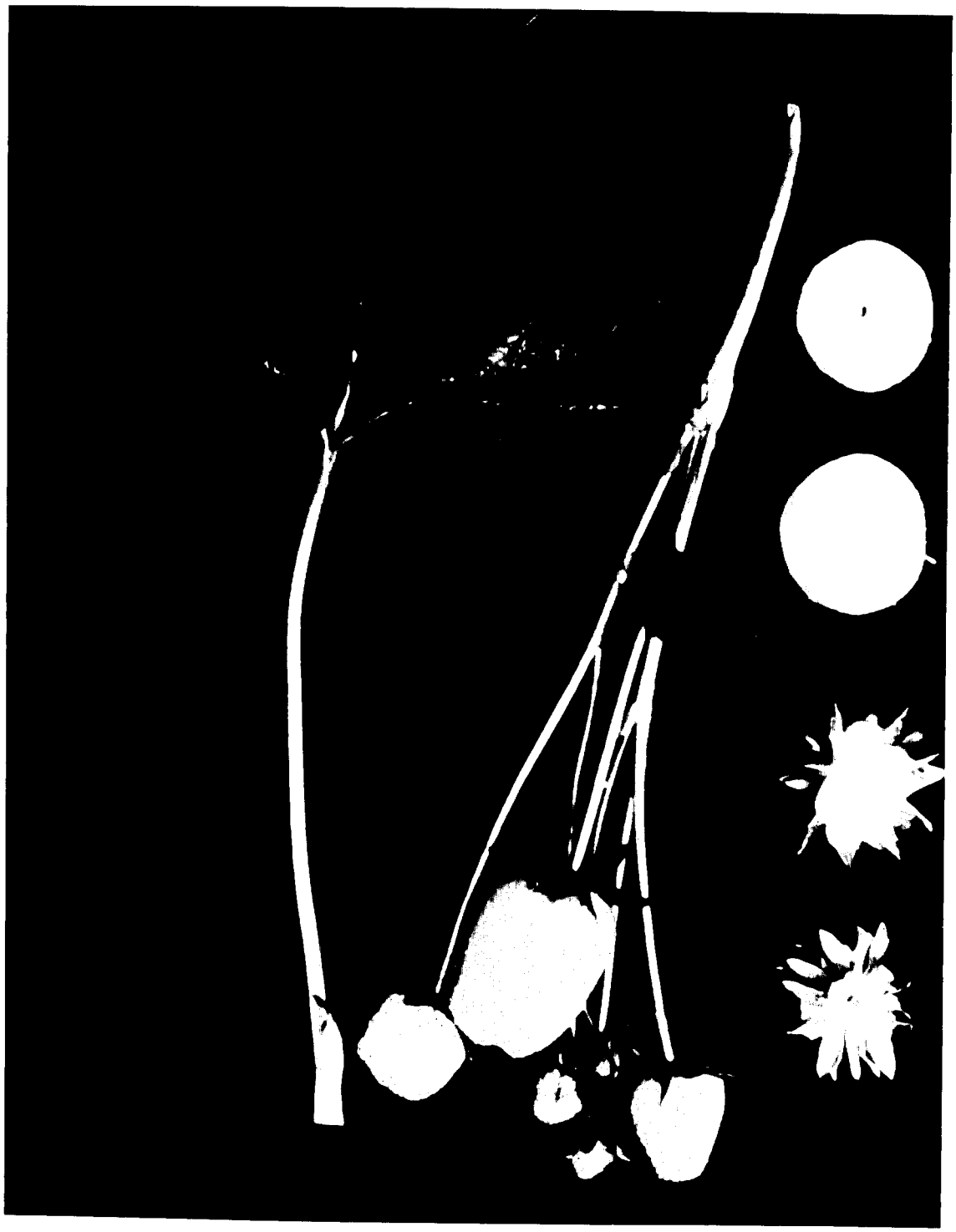

United States Patent [19]

Johnson, Jr.

[11] Plant 4,573

[45] Jul. 15, 1980

[54] STRAWBERRY PLANT

[75] Inventor: Harold A. Johnson, Jr., Watsonville, Calif.

[73] Assignee: Driscoll Strawberry Associates, Inc., Watsonville, Calif.

[21] Appl. No.: 27,194

[22] Filed: Apr. 4, 1979

[51] Int. Cl.[3] ..... A01H 5/03

[52] U.S. Cl. ..... Plt./48

[58] Field of Search ..... Plt./48

*Primary Examiner*—Robert E. Bagwill

[57] ABSTRACT

A new and distinct variety of strawberry plant characterized by its wedge shaped primary and secondary berries of greater length than width. The plant is distinguished by its large calyx and overlapping sepals. Its leaflets show a somewhat pointed apex at the margin rather than being rounded. Firmness of the berries are also distinguishing and have consistent fruit size. The variety is also characterized by the semi-openness of the plants throughout the season with fruit always accessible to pickers.

1 Drawing Figure

This invention relates to a new and distinct variety of the strawberry plant known as H9 and which is the result of a cross of the Driscoll Strawberry Associates selection G4, U.S. Plant Pat. No. 3,286, and the Driscoll Strawberry Associates selection GI.

The seedlings resulting from the aforementioned cross were grown and asexually multiplied by runners in Shasta County, Calif., and tested in the fruiting beds on the property of member growers of Driscoll Strawberry Associates, Inc. Clones of the seedlings were also held at the Propagation Nursery in Shasta County. One plant was selected from the aforementioned group of seedlings and further asexually reproduced in the Shasta County Nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

FIG. 1 of the accompanying drawing illustrates plant parts of the new variety, typical in size, shape and color.

A berry shown in cross section, illustrates flesh color and characteristic core cavity. The inflorescence pictured illustrates typical branching and relative size during June in the Watsonville area. The pedicel holding the primary berry originates from the axial of peduncles but may also originate near the union of the peduncles. The ripe wedge shaped primary and secondary berries illustrated are typical of this variety with the length usually greater than the width. The large calyx with overlapping sepals are also characteristic. The leaf illustrated is also typical, with the leaflet nearest the left of the illustration showing a somewhat pointed apex at the margin rather than a rounded margin. The strong petiole shown is almost always void of bracts.

This novel new summer planted spring variety is adapted mainly for use in central California. In test plot evaluations it has distinguished itself due to the firmness of the berry, as well as the high appearing gloss, red shape and large calyx.

For a summer planted variety, it produces relatively uniformly throughout the fruiting season with very few peaks and valleys to its production cycle. This production starts in May and continues throughout the fruiting season. The variety is also unique in that it stays semi-open throughout the season with the fruit always accessible to pickers. Fruit firmness remains throughout the summer period. Fruit size also remains consistent.

The plant of this new variety is generally smaller than the Driscoll Associates variety H4, U.S. Plant Pat. No. 3,987. It is also more open, not as dense as H4. Individual leaflets are slightly darker than H4 and individual leaflets are equal to or larger than H4. Individual petioles may be thicker and more erect than those of H4. The production cycle of the new variety is more consistent throughout the year than H4. H4 generally has a heavier production earlier than the new variety. The new variety varies from H4 in that it has a more wedge shaped berry and the epidermis is more consistently firm than that of H4, even though the seeds are not as exerted as H4. The new variety also has a more consistent gloss to the fruit than that of H4. The calyx of the new variety is consistently larger than that of H4. The flavor of the new variety is equal to or superior to that of H4 and the aroma is indistinguishable from H4. The new variety has moderate tolerance to mildew and based on limited observations is equal to H4 in susceptibility to two-spotted mite, *Mycospharella leafspot* and the red stele disease.

The new variety is not considered as prolific a runner producer as that of H4 at the nursery or the fruiting beds. As a seedling and a selection this new variety withstood natural invasions of certain virus components found in central California without losing its ability to produce. The varietal characteristics of the novel plant described below in detail were observed during the first fruiting season in the central coast region which is near the Pacific Ocean. The drawing was taken in Salinas during the month of June and specific measurements were taken mainly in the months of June, July and August. The color terminology as used herein is in accordance with Ridgeway's Color Standards and Nomenclature (1912 Edition).

Plants: Small to medium, not dense but semi-open with fruit accessable to pickers. It has an extensive root system.

Isozymes in Leaf Extracts — *Phosphoglucose isomerase* (PGI): H9 gave single banded pattern at 35 mm. identical to Tioga, a University of California introduction with the provisional monohybrid genotype 35/35 35/35 35/35 35/35 (Scandolios. 1969 Biochem. Genet. 3:37-79).

Leaflets:

*Medium to large in size.*—Center leaflet mostly 6 to 8 cm. in length and width. Total length of petiole and leaflet 20 to 30 cm. Color of upper side of leaflet, YEW green, Plate 31.

Runners: Runners are vigorous and abundant both at the nursery and fruiting beds.

Inflorescence:

*Medium to long in length.*—Mostly 20 to 30 cm. During mid-summer period pedicle holding primary berry may originate from the axil of peduncles or from one of the peduncles close to the axil. Flowers usually visible above the plant and anthers produce an abundance of pollen even early in the spring. Hair on tertiaries 20 mm. from berries is parallel to the pedicle. Tertiary pedicles are often fused together.

Fruit:

*Primaries are medium in size.*—35 to 40 mm. in length and width but length usually greater than width. Fruit has a high gloss appearance and is considered quite firm, both the flesh and epidermis. Size is relatively consistent throughout fruiting season. Secondary and tertiaries do drop off in size but meet minimum size of shipping standards. Fruit shape is mainly medium to long wedge (USDA Bulletin 1043) in outline with some berries at apex nearing the width of that at the calyx end of the fruit. Secondary and tertiary berries may become conic. Cockscombing appearance at the apex of wedge shaped berries is common when observing primaries. Shoulders of the fruit near the calyx are rounded, not necked. Except for the first berries in the spring, the fruit colors are consistent. The surface of fruit is smooth, not ridged or irregular in cutline. The seed is generally held equal to fruit surface or may be slightly inserted or exerted. Color of fruit surface, Carmen, Plate I, color of flesh, Nopal Red, Plate I. The core is small to medium.

Calyx:

*Mostly clasping not reflexed and large in diameter in relationship to fruit size.*—Primaries are 40 to 45 mm. in diameter. Individual sepals are often deeply serrated and are overlapping. Color of sepals on side facing fruit, Cress Green, Plate XXXI.

Seed:

*Small to medium in size, abundant and evenly spaced.*—Yellow but becoming dark when exposed to full sun.

I claim:

1. The new and distinct variety of strawberry plant herein described and illustrated, and identified by the characteristics enumerated above.

* * * * *